US009089638B2

(12) United States Patent
Kiyono et al.

(10) Patent No.: US 9,089,638 B2
(45) Date of Patent: Jul. 28, 2015

(54) MEDICAL NEEDLE DEVICE

(75) Inventors: Takafumi Kiyono, Hiroshima (JP);
Takayuki Ohno, Miyoshi (JP);
Takahide Nakanishi, Miyoshi (JP);
Toru Fukushima, Izumo (JP); Eiji Sanada, Miyoshi (JP)

(73) Assignee: JMS CO., LTD., Hiroshima-shi, Hiroshima (JP)

( * ) Notice: Subject to any disclaimer, the term of this patent is extended or adjusted under 35 U.S.C. 154(b) by 1074 days.

(21) Appl. No.: 12/442,097

(22) PCT Filed: Sep. 18, 2007

(86) PCT No.: PCT/JP2007/068088
§ 371 (c)(1),
(2), (4) Date: Mar. 19, 2009

(87) PCT Pub. No.: WO2008/035675
PCT Pub. Date: Mar. 27, 2008

(65) Prior Publication Data
US 2010/0049139 A1   Feb. 25, 2010

(30) Foreign Application Priority Data

Sep. 19, 2006  (JP) ................................. 2006-252286
Sep. 14, 2007  (JP) ................................. 2007-239640

(51) Int. Cl.
*A61M 5/158*    (2006.01)
*A61M 5/32*     (2006.01)
*A61M 25/06*    (2006.01)

(52) U.S. Cl.
CPC .............. *A61M 5/158* (2013.01); *A61M 5/3275* (2013.01); *A61M 25/0612* (2013.01); *A61M 25/0637* (2013.01); *A61M 5/3202* (2013.01); *A61M 5/3243* (2013.01)

(58) Field of Classification Search
CPC . A61M 25/02; A61M 5/178; A61M 25/0637; A61M 2025/0293; A61M 2025/024; A61M 5/32; A61M 5/3204; A61M 2005/3206; A61M 5/3275
USPC .................................. 604/174, 177–180, 263
See application file for complete search history.

(56) References Cited

U.S. PATENT DOCUMENTS 3,713,442 A   1/1973  Walter
4,250,880 A   2/1981  Gordon
(Continued)

FOREIGN PATENT DOCUMENTS

EP        1440702 A1    7/2004
JP        52-73590      6/1977
(Continued)

OTHER PUBLICATIONS

English Language International Search Report dated Oct. 23, 2007 issued in parent Appln. No. PCT/JP2007/068088.
(Continued)

*Primary Examiner* — Andrew Gilbert
*Assistant Examiner* — Matthew A Engel
(74) *Attorney, Agent, or Firm* — Holtz, Holtz, Goodman & Chick PC

(57) ABSTRACT

A medical needle device includes a hub having an injection needle fixed at a top end thereof, and a substantially cylindrical sheath which is fit on the hub and having a pair of wings mounted on both sides thereof. The pair of wings are bent along the both sides of the sheath, overlapped and held together at a time of puncturing so that an inner peripheral surface of the sheath strongly presses an outer peripheral surface of the hub, thereby preventing movement of the hub caused by transfer of the hub relative to the sheath both in a rotational direction and a longitudinal direction. sheath has a plurality of protrusions provided on the inner peripheral surface thereof in a circumferential direction, the protrusions being spaced out from each other; and the outer peripheral surface of the hub abuts the protrusions.

6 Claims, 13 Drawing Sheets

(56) References Cited

U.S. PATENT DOCUMENTS

| | | | |
|---|---|---|---|
| 7,377,911 B2 | 5/2008 | Kunitomi et al. | |
| 2004/0147882 A1* | 7/2004 | Kunitomi et al. | 604/263 |
| 2004/0236287 A1* | 11/2004 | Swenson et al. | 604/263 |
| 2004/0249346 A1 | 12/2004 | Kunitomi et al. | |
| 2008/0195059 A1* | 8/2008 | Sudo et al. | 604/239 |

FOREIGN PATENT DOCUMENTS

| | | |
|---|---|---|
| JP | 55-501090 A | 12/1980 |
| JP | 61-29748 U | 2/1986 |
| JP | 2001-293087 A | 10/2001 |
| JP | 2003-116991 A | 4/2003 |

OTHER PUBLICATIONS

Written Opinion of the International Searching Authority (English Translation and Japanese Language) issued in parent Appln. No. PCT/JP2007/068088.

Extended European Search Report dated Jun. 18, 2010 (in English) issued in counterpart European Application No. 07828241.5.

* cited by examiner though a pair of wings 21, 22 are fastened as described in (3), certain rotational torque is required between the hub 10 and the sheath 20 so as to prevent unexpected rotation of the injection needle 11 during the medical treatment. In addition, smooth rotation between the hub 10 and the sheath 20 is also required so as to adjust the position of the needle at the time of positional adjustment of the needle as described in (4).

MEDICAL NEEDLE DEVICE

This application is a U.S. National Phase Application under 35 USC 371 of International Application PCT/JP2007/068088 filed Sep. 18, 2007.

TECHNICAL FIELD

The present invention relates to medical needle devices with wings to be fastened on the patient's skin with adhesive tape, which are used for measures such as infusions or blood transfusions, or extracorporeal blood circulation.

BACKGROUND OF THE INVENTION

For measures such as blood dialysis therapy, infusions or blood transfusions, or extracorporeal blood circulation, winged medical needle devices fastened on the patient's skin with adhesive tape are widely used.

Such medical needle devices, as shown in FIGS. 6 and 7, include a hub 10 having an injection needle 11 fixed at the top end 10a thereof and a substantially cylindrical sheath 20 having a pair of wings 21, 22 mounted on both sides thereof. The sheath 20 is fit on the hub 10 which is movable relative to the sheath 20 both in a rotational and a longitudinal direction.

The wing 21 has a convex 23 and a groove 24 formed thereon whereas the wing 22 has a groove 25 and a convex 26 formed thereon and when the wings 21 and 22 are overlapped, the convex 23 engages with the groove 25 whereas the convex 26 engages with the groove 24.

The injection needle 11 is capped with a protective cap 30. The hub 10 has a tube 40 for infusions or blood transfusions connected to a rear end 10b thereof.

The hub 10, the sheath 20 and the tube 40 are respectively made of PC (polycarbonate), PE (polyethylene) and PVC (polyvinyl chloride). As shown in FIG. 8, the hub 10 having the sheath 20 fit thereon then has the tube 40 connected to the rear end 10b thereof. Further, the resultant hub 10 with the sheath 20 and the tube 40 is subjected to a heat treatment for "blocking adhesion".

The "blocking adhesion" is an adhesive technique to attain a chemically reinforced adhesive structure at an interface between the PC material and the PVC material for the effect of a plasticizer of the PVC material, obtained by applying thermal load on the PC material and the PVC material in a state in which the PC material abuts the PVC material.

The following will explain how to use the above-structured medical needle device.

(1) A pair of wings 21, 22 mounted on the both sides of the sheath 20 are held together in such a manner that the wings are pinched with a thumb and a forefinger as operation fingers so as to be closed as shown in FIG. 9. More specifically, a pair of the wings 21, 22 are bent along the both sides of the sheath 20, overlapped and maintained. The respective surfaces of a pair of the wings 21, 22 are overlapped, in which the convex 23 engages with the groove 25 and the convex 26 engages with the groove 24 so that the wing 21 and 22 are overlapped.

(2) The injection needle 11 is set on a blood vessel of a patient and then the blood vessel is secured.

(3) A pair of the wings 21, 22 are spread apart so as to come into contact with the patient's skin and are fastened on the patient's skin with adhesive tape (not shown).

(4) The injection needle 11 is rotated so as to be adjusted on a position where blood flow is more than any other position.

(5) After medical treatment, the injection needle 11 is removed from the patient's skin and the medical needle device is disposed.

In the course of puncturing described in (1) and (2), movement of the hub 10, caused by transfer of the hub 10 relative to the sheath 20 both in the rotational direction and the longitudinal direction has to be prevented. In order to achieve prevention of the movement of the hub 10, at the time of the puncturing, the wings 21, 22 clasp both sides of the sheath 20 so that the inner peripheral surface of the sheath 20 strongly presses the outer peripheral surface of the hub 10, thereby increasing holding force to prevent the movement without fail.

On the other hand, once the wings 21, 22 are fastened as described in (3), certain rotational torque is required between the hub 10 and the sheath 20 so as to prevent unexpected rotation of the injection needle 11 during the medical treatment. In addition, smooth rotation between the hub 10 and the sheath 20 is also required so as to adjust the position of the needle at the time of positional adjustment of the needle as described in (4).

Therefore, conventional sheaths 20 have adopted a structure shown in FIGS. 10 to 14 in order to attain stable rotational torque except for the time of the puncturing. FIG. 10 and FIG. 11 are front views of the sheath 20 and FIG. 12 is a plane view of the sheath 20.

As shown in FIG. 10, base ends 21b, 22b of the wings 21, 22, mounted on the both sides of the sheath 20 are thinner than top ends 21a, 22a of the wings 21, 22 so that the wings 21, 22 can be easily bent along the both sides of the sheath 20. Then, at the time of the puncturing, the wings 21, 22 are overlapped as shown in FIG. 11.

The sheath 20 has an annular protrusion 9 projecting inward provided in a circumferential direction thereof. FIG. 13 is a I-I line enlarged cross-section of FIG. 12 and FIG. 14 is a II-II line enlarged cross-section of FIG. 12. FIG. 13 and FIG. 14 show the hub 10 in a two-dot chain line.

Except for the time of the puncturing, such as in the course of medical treatment, the annular protrusion 9 abuts the outer peripheral surface of the hub 10, thereby generating the certain rotational torque so as to prevent the unexpected rotation of the injection needle 11. In addition, such a structure also enables the smooth rotation between the hub 10 and the sheath 20 so as to adjust the position of the needle at the time of positional adjustment of the needle.

Another example of the ordinary medical needle devices has projections formed on the surface of the base ends 21b, 22b of the wings 21, 22 while having bores formed on both sides of the sheath 20 so as to insert the projections on the wings 21, 22 into the bores on the sheath 20 and pressure the hub 10 with the top ends of the projections in order to increase the holding force at the time of the puncturing (see, for example, the Japanese unexamined Patent Publications No. 2001-293087 and 2003-116991).

The ordinary medical needle devices shown in FIGS. 6 to 14, however, have a problem that, in case a plurality of products are produced, each product varies in the rotational torque which generates between the hub 10 and the sheath 20 and some of the products are excessively increased in the rotational torque.

The problem is caused by the heat treatment aiming at "blocking adhesion", which is carried out in a manufacturing process of the medical needle devices.

In the heat treatment, thermal distribution inside a heat treatment apparatus varies, therefore, in case a plurality of assembled parts are heat treated, thermal load to be loaded on each assembled part, varies depending on where inside the heat treatment apparatus the assembled parts are positioned. Since the sheath 20 is made of PE which contracts for the heat treatment, the higher the temperature of the position where the medical needle device is arranged, the smaller a diameter of the inner peripheral surface of the resultant sheath 20 becomes so that the rotational torque between the hub 10 and the resultant sheath 20 increases for the effect of the friction. Accordingly, each of the resultant products have respective degrees of contraction thereby varying in the rotational torque, some of which result in products with an excessive rotational torque.

In addition, the annular protrusion 9 on the inner peripheral surface of the sheath 20 deforms from a circular shape along the hub 10 into an indeterminate shape for the effect of the heat treatment thereby increasing the rotational torque, which causes variety in the rotational torque because of the difference in treatment temperature.

Variety in the rotational torque, which causes difference in operability is not favorable. Especially, resultant products having the rotational torque higher than upper limit of a standard value (a value calculated in consideration of the operability) are not usable.

Accordingly, conventional medical needle devices have necessitated a very strict control of the temperature inside the heat treatment apparatus so as to prevent variety in the rotational torque. Therefore, there has been a strong demand for medical needle devices of which the rotational torque is hardly affected even in case they are heat treated at rather high temperatures.

The inventions disclosed in said Japanese unexamined Patent Publications have improved holding force at the time of the puncturing but have not prevented increase in the rotational torque except for the time of the puncturing or the variety in the rotational torque.

Therefore, the present invention aims at solving the above-mentioned problems, more specifically, an object of the present invention is to provide medical needle devices of which the rotational torque between the hub and the sheath is decreased and variety in the rotational torque is controlled.

DISCLOSURE OF THE INVENTION

In order to solve the above-mentioned problems, a first aspect of the invention provides a medical needle device comprising: a hub (10) having an injection needle (11) fixed at a top end (10*a*) thereof; and a substantially cylindrical sheath (20) which is fit on the hub (10) and having a pair of wings (21, 22) mounted on both sides thereof, said pair of wings (21, 22) being bent along the both sides of said sheath (20), overlapped and held together at a time of puncturing so that an inner peripheral surface of said sheath (20) strongly presses an outer peripheral surface of said hub (10) thereby preventing movement of said hub (10), caused by transfer of the hub (10) relative to said sheath (20) both in a rotational direction and a longitudinal direction, wherein: said sheath (20) has a plurality of protrusions (1) provided on the inner peripheral surface thereof in a circumferential direction, said protrusions (1) being spaced out from each other; and the outer peripheral surface of said hub (10) abuts said protrusions (1).

A second aspect of the invention provides a medical needle device according to the first aspect of the invention, wherein: said sheath (20) is fit on said hub (10) first: and then a tube (40) is adhered to a rear end (10*b*) of said hub (10) by means of heat treatment.

A third aspect of the invention provides a medical needle device according to the second aspect of the invention, wherein: said sheath (20) radially contracts when the tube (40) is adhered to the rear end (10*b*) of said hub (10) by means of the heat treatment; said protrusions (1) keep height (60) sufficient for abutting the outer peripheral surface of said hub (10) both before and after said heat treatment; and diameter (70) of the inner peripheral surface of said sheath (20) keeps a size which does not abut the outer peripheral surface of said hub (10) both before and after said heat treatment.

A fourth aspect of the invention provides a medical needle device according to any one of the first to the third aspects of the invention, wherein: said sheath (20) has said protrusions (1) provided on the inner peripheral surface thereof at regular intervals.

A fifth aspect of the invention provides a medical needle device according to any one of the first to the fourth aspects of the invention, wherein: said protrusions (1) are provided on symmetrical positions relative to a perpendicular line (90) which splits the inner peripheral surface of said sheath (20) equally into two parts to the left and to the right.

A sixth aspect of the invention provides a medical needle device according to any one of the first to the fifth aspects of the invention, wherein: said protrusions (2) are provided on a right side and a left side of the most extended positions on the inner peripheral surface of said sheath (20).

A seventh aspect of the invention provides a medical needle device according to any one of the first to the sixth aspects of the invention, wherein: said sheath (20) has said protrusions (4,5) provided on a plurality of positions which are spaced out from each other in a longitudinal direction on the inner peripheral surface thereof.

A eighth aspect of the invention provides a medical needle device according to any one of the first to the seventh aspects of the invention, wherein: a cross sectional shape of the outer peripheral surface of the hub (10) which said protrusions (1) abut is circular.

A ninth aspect of the invention provides a medical needle device according to any one of the first to the seventh aspects of the invention, wherein: said hub (10) which said protrusions (1) abut has a plurality of convexes (51, 52) formed along the outer peripheral surface thereof so that said protrusions (1) abut said convexes (51, 52) when said hub (10) transfers in a rotational direction relative to the sheath (20).

It is to be noted that the "outer peripheral surface" according to the ninth aspect of the invention does not include a plurality of convexes.

A tenth aspect of the invention provides a medical needle device according to ninth aspect of the invention, wherein: the cross sectional shape of the outer peripheral surface of said hub (10) which said protrusions (1) abut is a polygon of which each corner forms said plurality of convexes (51).

It is to be noted that the "outer peripheral surface" according to the tenth aspect of the invention includes each corner as a plurality of convexes.

An eleventh aspect of the invention provides a medical needle device according to the tenth aspect of the invention, wherein: said polygon is a regular polygon of which number of corners is a multiple of number of said protrusions (1) provided on the inner peripheral surface of said sheath (20) at regular intervals.

It is to be noted that the "multiple" according to the eleventh aspect of the invention includes fractional multiples from 0 to 1, not only integer multiples of 1 or more.

A twelfth aspect of the invention provides a medical needle device according to eleventh aspect of the invention, wherein: said polygon is a regular dodecagon; and the number of said protrusions (1) is six.

A thirteenth aspect of the invention provides a medical needle device according to any one of ninth to twelfth aspects of the invention, wherein: said convexes (51) have projecting height which does not abut the inner peripheral surface of said sheath (20) in a state in which said protrusions (1) do not abut said convexes (51).

A fourteenth aspect of the invention provides a medical needle device according to any one of ninth to twelfth aspects of the invention wherein: said convexes (52) have the projecting height which abuts the inner peripheral surface of said sheath (20) in the state in which said protrusions (1) do not abut said convexes (52).

A fifteenth aspect of the invention provides a medical needle device according to any one of ninth to fourteenth aspects of the invention, wherein: the projecting height and elastic force of said convexes (51, 52) prevent said hub (10) from rotating relative to said sheath (20) in case rotational torque less than certain amount T is applied on the hub (10) in a state in which said protrusions (1) abut said convexes (51, 52) whereas the projecting height and the elastic force of said convexes (51, 52) allow said protrusions (1) to climb over said convexes (51, 52) so that said hub (10) rotates relative to said sheath (20) in case the rotational torque not less than the certain amount T is applied on the hub (10) in the state in which said protrusions (1) abut said convexes (51, 52).

Symbols in parentheses show constituents or items corresponding to BEST MODE FOR CARRYING OUT THE INVENTION and DRAWINGS.

According to the medical needle device according to the first aspect of the present invention, the substantially cylindrical sheath fit on the hub has a plurality of protrusions which are spaced out from each other provided on the inner peripheral surface thereof in the circumferential direction so that the outer peripheral surface of said hub abuts the protrusions. Such a structure prevents movement of the hub, caused by transfer of the hub relative to the sheath both in the rotational direction and the longitudinal direction for the effect of frictional resistance which generates between the outer peripheral surface of the hub and the protrusions on the sheath. In addition, when force is applied on the hub from outside, the hub can rotate with an appropriate rotational torque applied thereon.

On the other hand, at the time of puncturing, a pair of the wings mounted on both sides of the sheath are bent along the both sides of the sheath, overlapped and held together so that the inner peripheral surface of the sheath strongly presses the outer peripheral surface of the hub thereby preventing the movement of the hub, caused by transfer of the hub relative to the sheath both in the rotational direction and the longitudinal direction without fail.

According to the medical needle device according to the second aspect of the present invention, in a production process of the medical needle device, the sheath is fit on the hub first and then the tube is adhered to the rear end of the hub by means of the heat treatment, which may cause deformation of the protrusions on the sheath and increase in the rotational torque. But a plurality of protrusions on the sheath according to the present invention are spaced out from each other, which absorb the deformation caused by the heat treatment in a different manner from the ordinary annular protrusion, thereby hardly affecting the rotational torque. Accordingly, in addition to the effect of the first aspect of the invention, the medical needle device according to the present invention is prevented both from the increase in the rotational torque, caused by the heat treatment, and variety in the rotational torque, caused by the difference in heat treatment temperature.

According to the medical needle device according to the third aspect of the present invention, the sheath radially contracts at the time of the heat treatment whereas the protrusions on the sheath keep the height sufficient for abutting the outer peripheral surface of the hub both before and after the heat treatment. Accordingly, in addition to the effect of the second aspect of the invention, idling between the hub and the sheath is prevented even before the heat treatment, not to mention after the heat treatment, so that assembly process is smoothly carried out.

In addition, the diameter of the inner peripheral surface of the sheath keeps the size which does not abut the outer peripheral surface of the hub both before and after the heat treatment. Therefore, the friction does not generate between the inner peripheral surface of the sheath and the outer peripheral surface of the hub even after the heat treatment, not to mention before the heat treatment, so that the rotational torque does not increase. Accordingly, the increase in the rotational torque, caused by the heat treatment, is prevented and the variety in the rotational torque, caused by the difference in the heat treatment temperature, is controlled.

According to the medical needle device according to the fourth aspect of the present invention, in addition to the effect of any one of the first to the third aspects of the invention, since the sheath has the protrusions provided on the inner peripheral surface thereof at regular intervals, the protrusions on the inner peripheral surface stably hold the outer peripheral surface of the hub.

According to the medical needle device according to the fifth aspect of the present invention, the protrusions on the sheath are provided on symmetrical positions relative to the perpendicular line which splits the inner peripheral surface of the sheath equally into two parts to the left and to the right. Therefore, when the wings on the sheath are overlapped and held together so that the inner peripheral surface of the sheath strongly presses the outer peripheral surface of the hub, in addition to the effect of any one of the first to the fourth aspects of the invention, the inner peripheral surface of the sheath equally presses the left side and the right side of the outer peripheral surface of the hub.

According to the medical needle device according to the sixth aspect of the present invention, the protrusions on the sheath are provided on the right side and the left side of the most extended positions on the inner peripheral surface of the sheath. Therefore, when the wings on the sheath are overlapped and held together so that the inner peripheral surface of the sheath strongly presses the outer peripheral surface of the hub, in addition to the effect of any one of the first to the fifth aspects of the invention, pressing force can be accurately transmitted.

According to the medical needle device according to the seventh aspect of the present invention, the sheath has the protrusions provided on a plurality of positions which are spaced out from each other in a longitudinal direction on the inner peripheral surface thereof. Therefore, in addition to the effect of any one of the first to the sixth aspects of the invention, the protrusions on the sheath abut the outer peripheral surface of the hub at a plurality of the positions in the longitudinal direction, thereby stably holding the hub.

According to the medical needle device according to the eighth aspect of the present invention, in addition to the effect of any one of the first to the seventh aspects of the invention, the cross sectional shape of the outer peripheral surface of the hub which the protrusions abut is circular, which generates the same fitting force between the protrusions and anywhere all around 360 degrees of the outer peripheral surface for the effect of the same friction therebetween.

According to the medical needle device according to the ninth aspect of the present invention, the hub which the protrusions abut has a plurality of the convexes formed along the outer peripheral surface thereof so that the protrusions abut the convexes when the hub transfers in the rotational direction relative to the sheath. Therefore, when the force is applied on the hub relative to the sheath in the rotational direction, in addition to the effect of any one of the first to the seventh aspects of the invention, the protrusions in point contact with the outer peripheral surface of the hub abut the convexes formed outward compared with the outer peripheral surface of the hub so that the fitting force increases for the effect of the projection of the convexes, thereby increasing the rotational torque.

Such a structure prevents unexpected rotation of the hub relative to the sheath, caused by weight of a forceps which fastens the tube for infusions or blood transfusions, connected to the rear end of the hub so as to blockade watercourse of the tube.

According to the medical needle device according to the tenth aspect of the present invention, the cross sectional shape of the outer peripheral surface of the hub, which the protrusions abut is the polygon of which each corner forms a plurality of convexes. Accordingly, a rotational operation is carried out by rotating the hub relative to the sheath so that the protrusions abut the convexes and applying further force in the rotational direction so that the convexes press the protrusions in an outward direction and then the protrusions climb over convexes and abut the adjacent convexes spaced out from the former convexes. As a result, in addition to the effect of the ninth aspect of the invention, the rotational torque (rotational operation force) not less than certain amount T required for climbing over the convexes is transmitted to the user as a tactile signal (sense of click). Specifically, corner-shaped convexes transmit a sharper tactile signal (sense of click) than round convexes without corners.

According to the medical needle device according to the eleventh aspect of the present invention, the polygon is the regular polygon of which number of the corners is the multiple of the number of the protrusions provided on the inner peripheral surface of the sheath at regular intervals. As a result, in addition to the effect of the tenth aspect of the invention, such a structure transmits the tactile signal (sense of click) at regular intervals at the time of the rotational operation.

According to the medical needle device according to the twelfth aspect of the present invention, the polygon is the regular dodecagon and the number of the protrusions is six, which transmits the tactile signal (sense of click) every rotational angle of 30 degrees. Accordingly, in addition to the effect of the tenth aspect of the invention, three consecutive times of the rotational operation of 30 degrees results in the accurate rotational operation of 90 degrees.

Some of the medical needle devices include a pull-back operational mechanism as an erroneous piercing prevention mechanism in which the hub having the injection needle fit on the top end thereof is rotated for 90 degrees relative to the sheath after use so as to match phase between convexes on the hub and concaves on the sheath and then pull back and stored the needle inside the sheath. The accurate rotational operation of 90 degrees, obtained by just performing three consecutive times of the rotational operation of 30 degrees with the tactile signals (sense of click) enables the medical needle devices with the pull-back operational mechanism to match the hub and the sheath accurately, safely and extremely easily on a certain position and pull back and store the injection needle inside the sheath.

According to the medical needle device according to the thirteenth aspect of the present invention, the convexes have the projecting height which does not abut the inner peripheral surface of the sheath in the state in which the protrusions do not abut the convexes whereas according to the medical needle device according to the fourteenth aspect of the present invention, in addition to the effect of any one of ninth to twelfth aspects of the invention, the convexes have the projecting height which abuts the inner peripheral surface of the sheath in the state in which the protrusions do not abut the convexes. Therefore, in addition to the effect of any one of ninth to twelfth aspects of the invention, fitting force between the protrusions and the convexes can be increased or decreased in the state in which the protrusions do not abut the convexes.

According to the medical needle device according to the fifteenth aspect of the present invention, the projecting height and the elastic force of the convexes prevent said hub from rotating relative to said sheath in case the rotational torque less than the certain amount is applied on the hub in the state in which the protrusions abut the convexes whereas the projecting height and the elastic force of the convexes allow the protrusions to climb over the convexes so that the hub rotates relative to the sheath in case the rotational torque not less than the certain amount is applied on the hub in the state in which the protrusions abut the convexes. Therefore, in addition to the effect of any one of ninth to fourteenth aspects of the invention, in case the certain amount T is set to be larger than weight of the forceps which fastens the tube for infusions or blood transfusions, connected to the rear end of the hub so as to blockade watercourse of the tube and larger than the force required for normal operation within a manually operatable range, unexpected rotation of the hub relative to the sheath, caused by the weight of the forceps is prevented and a manual operation of the user can obtain the fitting force of the hub with the sheath to the maximum on a point just before the certain amount T.

BEST MODE FOR CARRYING OUT THE INVENTION

Figure 1:
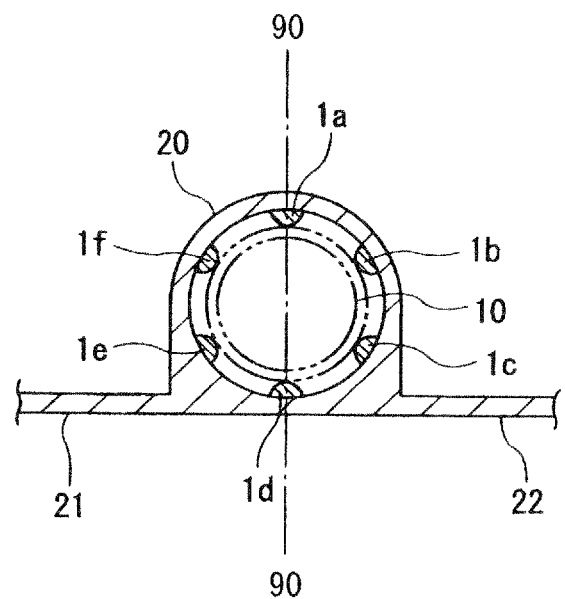
FIG. 1 is a cross section of a sheath of a medical needle device according to embodiment 1 of the present invention.

A medical needle device according to an embodiment of the present invention will be described.

The medical needle device according to the embodiment of the present invention includes, in the same manner as a medical needle device according to a prior art shown in FIG. 6 to FIG. 14, a hub 10 having an injection needle 11 fixed at the top end 10*a* thereof and a substantially cylindrical sheath 20 having a pair of wings 21, 22 mounted on both sides thereof. The sheath 20 is fit on the hub 10 which is movable relative to the sheath 20 both in a rotational direction and a longitudinal direction.

The wing 21 has a convex 23 and a groove 24 formed thereon whereas the wing 22 has a groove 25 and a convex 26 formed thereon, and when the wings 21 and 22 are overlapped, the convex 23 engages with the groove 25 whereas the convex 26 engages with the groove 24.

The injection needle 11 is capped with a protective cap 30 and a tube 40 for infusions or blood transfusions is connected to a rear end 10*b* of the hub 10.

Figure 8:
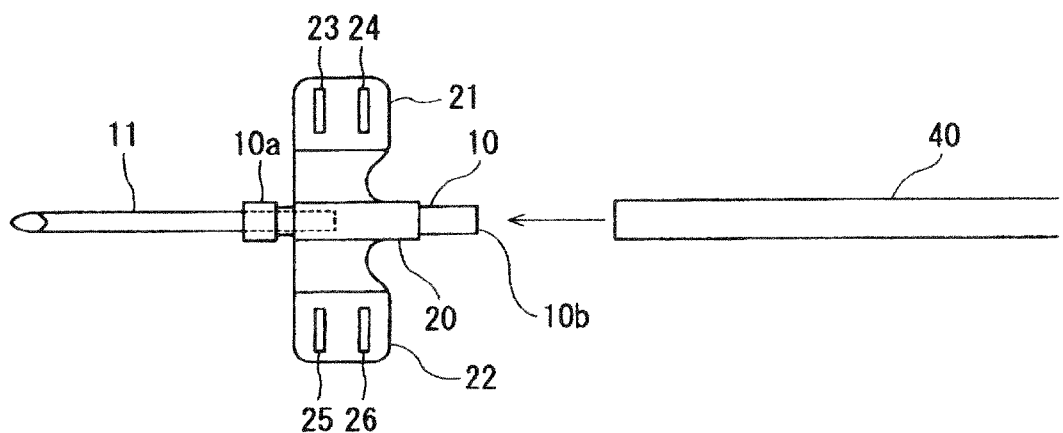
FIG. 8 is a plane view showing a method of assembling the medical needle device according to the prior art.

The hub 10, the sheath 20 and the tube 40 are respectively made of PC (polycarbonate), PE (polyethylene) and PVC (polyvinyl chloride). As shown in FIG. 8, the sheath 20 is fit on the hub 10, the tube 40 is connected to the rear end 10*b* of the hub 10 and the resultant medical needle device is subjected to a heat treatment as a "blocking adhesion".

The medical needle device according to the prior art has an annular protrusion 9 provided on an inner peripheral surface of the sheath 20 as shown in FIGS. 9 to 14 whereas the medical needle device according to the following embodiment has a plurality of protrusions which are spaced out from each other instead of the annular protrusion 9 provided on the inner peripheral surface of the sheath 20 in a circumferential direction.

Figure 2:
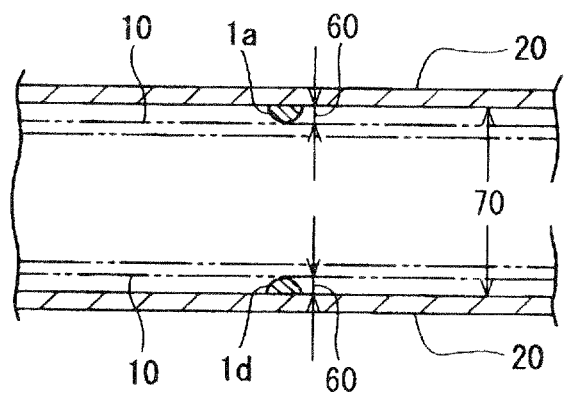
FIG. 2 is a longitudinal section of the sheath of the medical needle device according to embodiment 1 of the present invention.

Referring to FIG. 1 and FIG. 2, a medical needle device according to embodiment 1 will be described.

Figure 12:
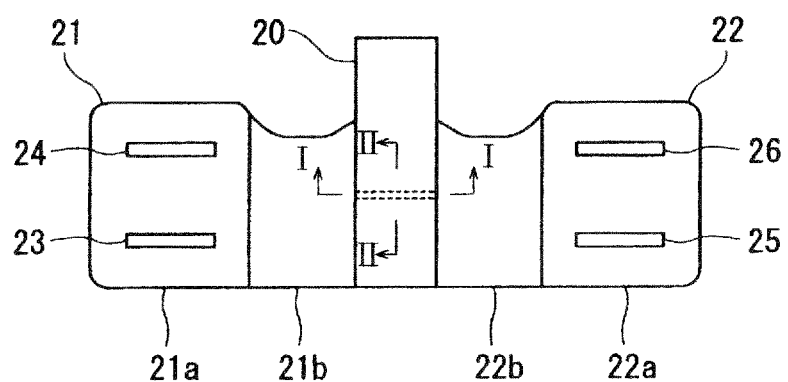
FIG. 12 is the plane view of the sheath of the medical needle device according to the prior art.
Figure 13:
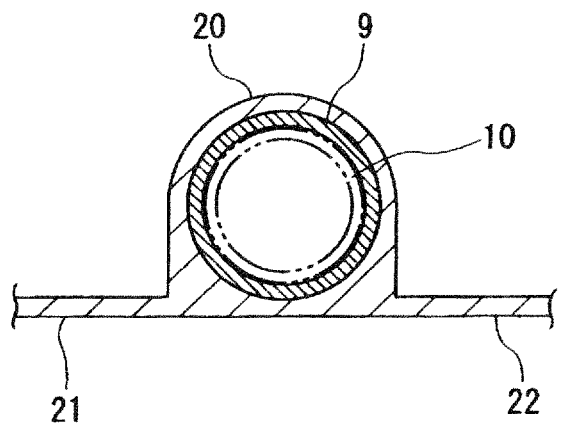
FIG. 13 is a I-I line enlarged cross section of FIG. 12.
Figure 14:
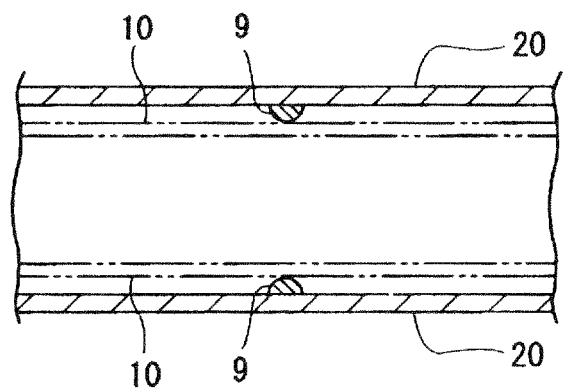
FIG. 14 is a II-II line enlarged cross section of FIG. 12.

FIG. 1 is a cross section of a sheath 20 of a medical needle device according to embodiment 1, which corresponds to a I-I line enlarged cross section of FIG. 12. FIG. 2 is a longitudinal section of the sheath 20, which corresponds to a II-II line enlarged cross section of FIG. 12.

As shown in FIG. 1 and FIG. 2, the sheath 20 has protrusions 1*a*, 1*b*, 1*c*, 1*d*, 1*e* and 1*f*, which are spaced out from each other (described as protrusions 1 hereinafter) provided on the inner peripheral surface thereof in the circumferential direction. The protrusions 1 are formed into cross-section semicircular shapes protruding inward from the inner peripheral surface of the sheath 20, vertexes of which abut an outer peripheral surface of the hub 10 inserted into the sheath 20.

The protrusions 1 are provided at regular intervals and on symmetrical positions relative to a perpendicular line 90 which splits the inner peripheral surface of the sheath 20 equally into two parts to the left and to the right.

Number of the protrusions according to the present embodiment is six but the number is not strictly restricted. It is to be noted that the number of the protrusions is preferably not less than three so as to sufficiently hold the outer peripheral surface of the hub 10.

The protrusions are not necessarily of semicircular shapes and may also be of conical shapes which are triangular in cross section or of cylindrical shapes which are rectangle in cross section. But the protrusions preferably have shapes of which as small areas as possible (including point contact) abut the outer surface of the hub 10.

Next, heat treatment for manufacturing the medical needle device according to the present embodiment will be described.

As shown in FIG. 8, the sheath 20 is fit on the hub 10 and then the tube 40 is connected to the rear end 10*b* of the hub 10, which are subjected to the heat treatment as the blocking adhesion. The heat treatment is carried out upon arranging the multiple assembled parts inside a heat treatment apparatus.

Since the sheath 20 is made of PE which contracts for the heat treatment, height 60 of the protrusions 1 and diameter 70 of the inner peripheral surface of the sheath 20 are adjusted as shown in FIG. 2 so that frictional resistance between the sheath 20 and the hub 10 is not greatly increased both before and after the heat treatment.

Specifically, the protrusions 1 have height 60 sufficient for abutting the outer peripheral surface of the hub 10 both before and after the heat treatment. That is, the height 60 of the protrusions 1 is adjusted so as to prevent idling between the hub and the sheath for the effect of the protrusions 1 even before the heat treatment, not to mention after the heat treatment.

In addition, the diameter 70 of the inner peripheral surface of the sheath 20 keeps the size which does not abut the outer peripheral surface of the hub 10 both before and after the heat treatment. That is, the diameter 70 is adjusted so as to prevent the friction between the inner peripheral surface of the sheath 20 and the outer peripheral surface of the hub 10 even after the heat treatment, not to mention before the heat treatment, thereby preventing increase in the rotational torque.

There still remains possibility that the protrusions 1 deform for the effect of the heat treatment so that the rotational torque increases. But protrusions 1 comprise a plurality of protrusions 1*a*, 1*b* 1*c*, 1*d*, 1*e* and 1*f*, which are spaced out from each other in a different manner from the ordinary annular protrusion 9 so that the protrusions 1 have reduced contact areas with the hub 10 and the spaces between the protrusions 1 absorb deformation caused by the heat treatment.

As mentioned above, adjustment of the height 60 of the protrusions 1 and the diameter 70 of the inner peripheral surface of the sheath 20 as well as the spaces between the protrusions 1 prevents increase in the rotational torque, caused by the heat treatment. Accordingly, even in case multiple assembled parts are arranged inside a heat treatment apparatus and heat treated, increase in the rotational torque caused by contraction of the sheath 20 hardly occurs and difference in treatment temperature of the multiple parts, caused by arranged positions of the multiple parts does not result in variety in the rotational torque.

Method of using the medical needle device of the present embodiment will be described hereinafter.

Figure 9:
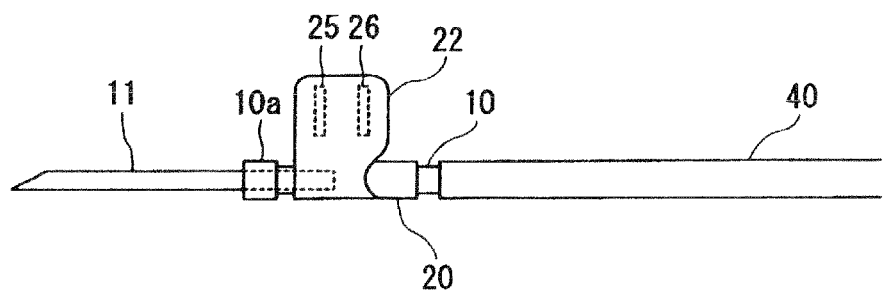
FIG. 9 is a lateral view showing a method of using the medical needle device according to the prior art.
Figure 10:
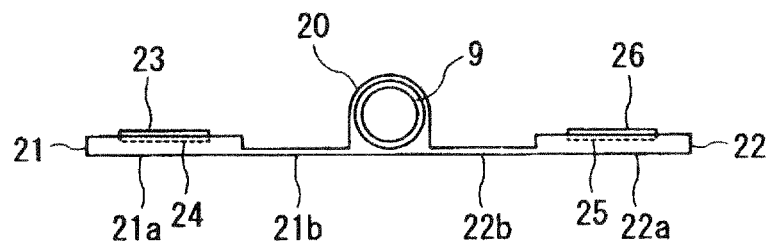
FIG. 10 is a front view of a sheath of the medical needle device according to the prior art.
Figure 11:
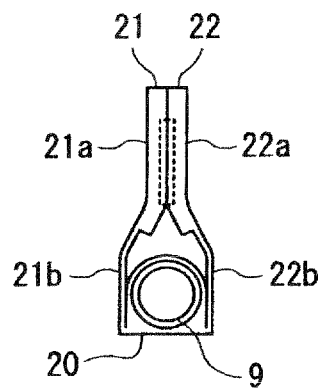
FIG. 11 is the front view of the sheath of the medical needle device according to the prior art (at the time of puncturing)

(1) The two wings 21, 22 mounted on the both sides of the sheath 20 are held together in such a manner that the wings are pinched with a thumb and a forefinger as operation fingers so as to be closed as shown in FIG. 9. More specifically, a pair of the wings 21, 22 are bent along the both sides of the sheath 20, overlapped and maintained. The respective surfaces of a pair of the wings 21, 22 are overlapped, in which the convex 23 engages with the groove 25 and the convex 26 engages with the groove 24 so as to prevent deflection between the wings 21, 22.

(2) The injection needle 11 is set on a blood vessel of a patient and then the blood vessel is secured.

In the course of puncturing described in (1) and (2), since the inner peripheral surface of the sheath 20 strongly presses the outer peripheral surface of the hub 10, movement of the hub 10, caused by transfer of the hub 10 relative to the sheath 20 both in the rotational direction and the longitudinal direction is completely prevented, which enables safe puncturing action.

(3) A pair of the wings 21, 22 are spread apart so as to come into contact with the patient's skin and are fastened with adhesive tape (not shown) on the patient's skin.

(4) The injection needle 11 is rotated so as to be adjusted on a position where blood flow is more than any other position.

After fastening the wings 21, 22 as described in (3), the protrusions 1 on the sheath 20 abut the outer peripheral surface of the hub 10 so that frictional resistance between the outer peripheral surface of the hub 10 and the protrusions 1 on the sheath 20 controls the movement of the hub 10, caused by the transfer of the hub 10 relative to the sheath 20 both in the rotational direction and longitudinal direction so as to prevent the injection needle 11 from coming off. In addition, such a structure enables to rotate the hub 10 for the effect of an appropriate rotational torque at the time of positional adjustment of the needle as described in (4).

(5) After medical treatment, the injection needle 11 is removed from the patient's skin and the medical needle device is disposed.

According to the medical needle device according to embodiment 1, the substantially cylindrical sheath 20 fit on the hub 10 has a plurality of protrusions 1 which are spaced out from each other provided on the inner peripheral surface thereof in the circumferential direction and the outer peripheral surface of the hub 10 abuts the protrusions 1. Such a structure prevents the movement of the hub 10, caused by the transfer of the hub 10 relative to the sheath 20 both in the rotational direction and the longitudinal direction for the effect of frictional resistance between the outer peripheral surface of the hub 10 and the sheath 20. Also when force is applied on the hub 10 from outside, the hub 10 can rotate for the effect of the appropriate rotational torque.

On the other hand, at the time of puncturing, a pair of the wings 21, 22 mounted on both sides of the sheath 20 are bent along the both sides of the sheath 20, overlapped and held together so that the inner peripheral surface of the sheath 20 strongly presses the outer peripheral surface of the hub 10 thereby preventing the movement of the hub 10, caused by the transfer of the hub 10 relative to the sheath 20 both in the rotational direction and the longitudinal direction without fail.

In addition, in the production process of the medical needle device, the sheath 20 is fit on the hub 10 first and then the tube 40 is adhered to the rear end 10b of the hub 10 by means of the heat treatment, which may cause the protrusions 1 on the sheath 20 to deform, thereby increasing the rotational torque. But a plurality of protrusions 1 on the sheath 20, including 1a, 1b 1c, 1d, 1e and 1f are spaced out from each other, which absorbs deformation caused by the heat treatment, thereby hardly affecting the rotational torque in a different manner from an ordinary annular protrusion 9. Accordingly, the medical needle device according to the present embodiment is prevented both from increase in the rotational torque, caused by the heat treatment and the variety in the rotational torque, caused by the difference in the heat treatment temperature.

The sheath 20 radially contracts at the time of the heat treatment whereas the protrusions 1 on the sheath 20 have height 60 sufficient for abutting the outer peripheral surface of the hub 10 both before and after the heat treatment. Accordingly, idling between the hub 10 and the sheath 20 is prevented even before the heat treatment, not to mention after the heat treatment, so that assembly process is smoothly carried out.

In addition, the diameter 70 of the inner peripheral surface of the sheath 20 keeps the size which does not abut the outer peripheral surface of the hub 10 both before and after the heat treatment. Therefore, the friction does not generate between the inner peripheral surface of the sheath 20 and the outer peripheral surface of the hub 10 even after the heat treatment, not to mention before the heat treatment, so that the rotational torque does not increase. Accordingly, increase in the rotational torque, caused by the heat treatment is prevented and the variety in the rotational torque, caused by the difference in the heat treatment temperature is controlled.

Further, since the sheath 20 has the protrusions 1 provided on the inner peripheral surface thereof at regular intervals, the protrusions 1 on the inner peripheral surface stably hold the outer peripheral surface of the hub 10.

Furthermore, the protrusions 1 on the sheath 20 are provided on symmetrical positions relative to the perpendicular line 90 which splits the inner peripheral surface of the sheath 20 equally into two parts to the left and to the right. Therefore, when the wings 21, 22 on the sheath 20 are overlapped and held together so that the inner peripheral surface of the sheath 20 strongly presses the outer peripheral surface of the hub 10, the inner peripheral surface of the sheath 20 equally presses the left side and the right side of the outer peripheral surface of the hub 10.

Figure 15:
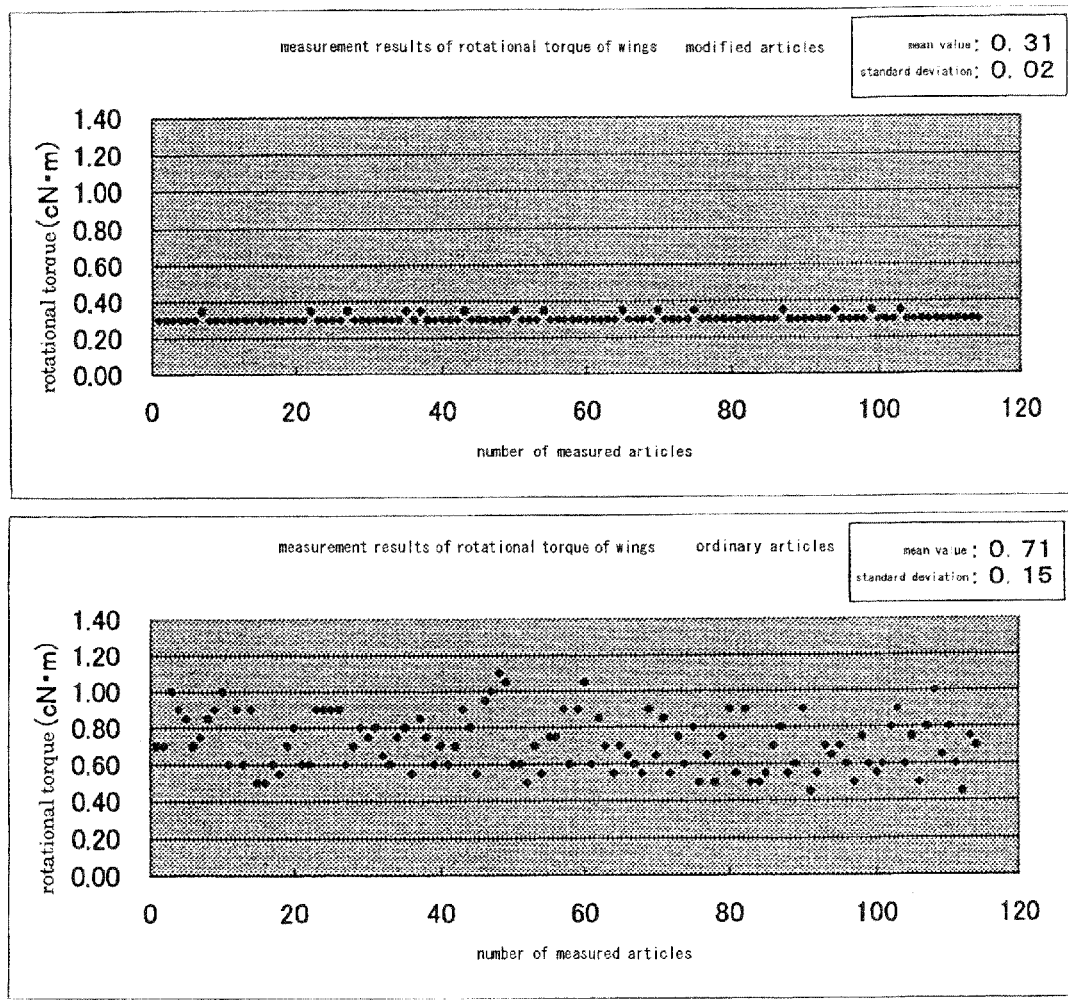
FIG. 15 is a figure showing results of measurement of rotational torque of the medical needle devices.

FIG. 15 shows results of measurement of rotational torque of plural medical needle devices according to the present embodiment and those according to a prior art.

In FIG. 15, "modified articles" on an upper column are the medical needle devices according to the present embodiment, of which the result of the measurement is shown therein whereas "ordinary articles" on a lower column are the medical needle devices according to the prior art, of which the result of the measurement is shown therein. The heat treatment was carried out for 60 minutes at a temperature of 96 degrees.

As shown in FIG. 15, the result of measurement of the rotational torque (the mean value±standard deviation) of the medical needle device of the prior art after the heat treatment is 0.71±0.15 cN·m which shows that ordinary articles on the whole are high in the rotational torque and wide in the variety in the rotational torque. On the other hand, the result of measurement of the rotational torque of the modified articles after the heat treatment is 0.31±0.02 cN·m which shows that the modified articles on the whole are low in the rotational torque and very narrow in the variety in the rotational torque. Accordingly, the result shows that a stable rotational torque is attained among a plurality of modified articles.

Some of the ordinary articles show remarkably high rotational torque even in case the articles are heat treated at the temperature of 93 degrees. On the other hand, as shown in FIG. 15, the modified articles are not varied in the rotational torque even in case the articles are heat treated at the temperature of 96 degrees, which enables to provide stable quality. In addition, the present invention enables to widen a range of heat treatment temperature and shorten heat treatment time.

Next, referring to FIG. 3, a medical needle device according to embodiment 2 will be described.

Figure 3:
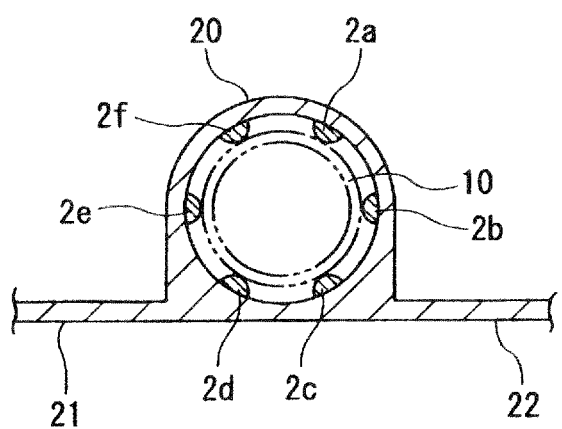
FIG. 3 is a cross section of a sheath of a medical needle device according to embodiment 2 of the present invention.

FIG. 3 is a cross section of the sheath 20 of a medical needle device according to embodiment 2, which corresponds to a I-I line enlarged cross section of FIG. 12.

The medical needle device according to embodiment 2 has protrusions 2a, 2b, 2c, 2d, 2e and 2f (described as protrusions 2 hereinafter) provided on the inner peripheral surface of the sheath 20. Among the protrusions 2, protrusions 2b and 2e are respectively provided on a right side and a left side of the most extended positions on the inner peripheral surface of the sheath. The most extended positions on the sheath 20 are the positions on which more force is applied than any other position on the sheath 20 when the wings 21, 22 are bent and pressed on both sides of the sheath 20.

Accordingly, since the medical needle device according to the embodiment 2 has the protrusions 2 provided on the right side and the left side of the most extended positions on the inner peripheral surface on the sheath 20, pressing force can be accurately transmitted when the wings 21, 22 on the sheath 20 are overlapped and held together so that the inner peripheral surface of the sheath 20 strongly presses the outer peripheral surface of the hub 10.

Next, referring to FIG. 4, a medical needle device according to embodiment 3 will be described.

Figure 4:
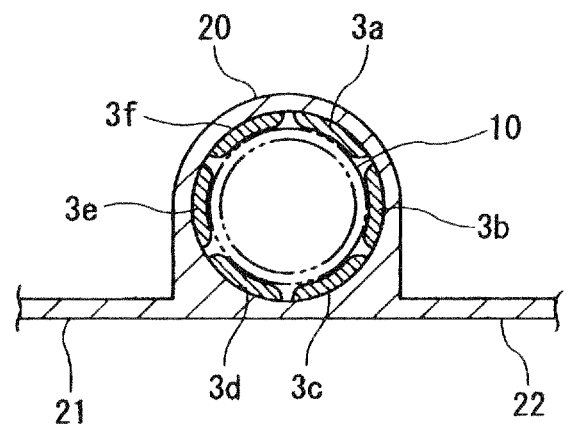
FIG. 4 is a cross section of a sheath of a medical needle device according to embodiment 3 of the present invention.

FIG. 4 is a cross section of the sheath 20 of a medical needle device according to embodiment 3, which corresponds to a I-I line enlarged cross section of FIG. 12.

The medical needle device according to embodiment 3 has protrusions 3a, 3b, 3c, 3d, 3e and 3f (described as protrusions 3 hereinafter) provided on the inner peripheral surface of the sheath 20. The protrusions 3 are larger in a circumferential direction than the protrusions 1 of the embodiment 1 or the protrusions 2 of the embodiment 2. Therefore, space between two adjacent protrusions 3 is narrow.

The protrusions 3 of the embodiment 3, larger in the circumferential direction, are inferior to the embodiment 1 or the embodiment 2 on points of increase or variety in the rotational torque since contact area between the protrusions 3 and the hub 10 is larger and deformation degree of the protrusions 3 at the time of the heat treatment deteriorates. But, as compared with an annular protrusion 9 of a prior art, the protrusions 3 are smaller in the contact area with the hub 10 and absorb the deformation caused by the heat treatment to some extent.

Next, referring to FIG. 5, a medical needle device according to embodiment 4 will be described.

Figure 5:
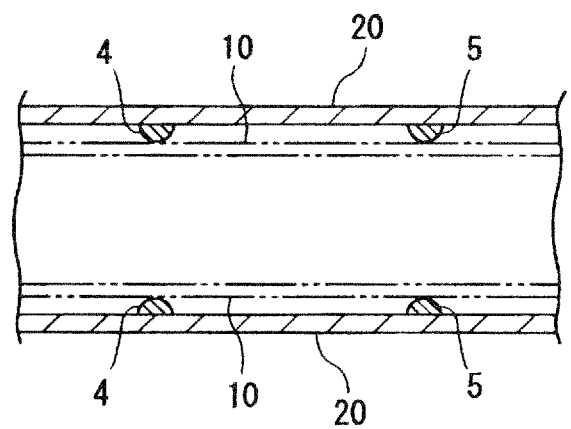
FIG. 5 is a longitudinal section of the sheath of the medical needle device according to embodiment 4 of the present invention.
Figure 6:
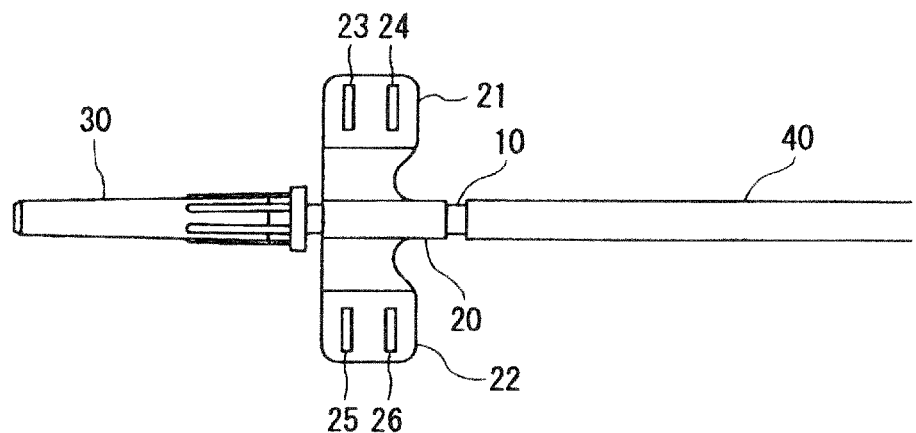
FIG. 6 is a plane view of a medical needle device according to a prior art.
Figure 7:
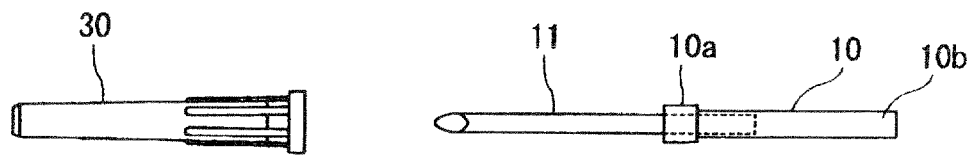
FIG. 7 is an exploded plane view of the medical needle device according to the prior art.
Figure 7:
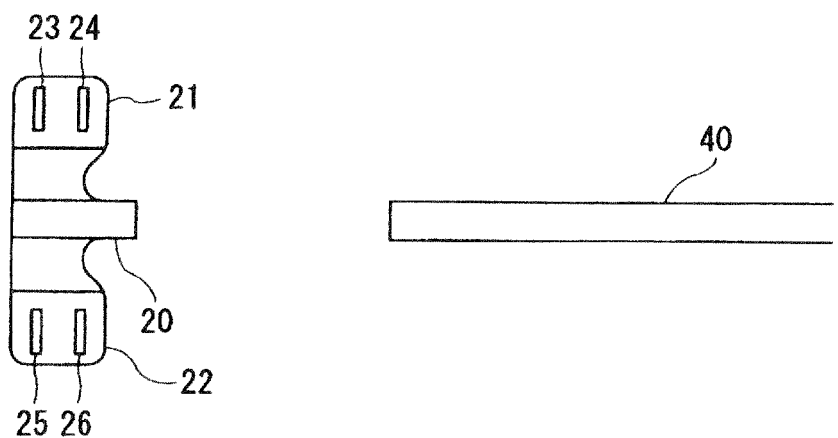

FIG. 5 is a longitudinal section of the sheath 20 of a medical needle device according to embodiment 4, which corresponds to a II-II line enlarged cross section of FIG. 12.

The medical needle device according to embodiment 4 has protrusions 4 and protrusions 5 provided on the inner peripheral surface of the sheath 20. More specifically, according to the embodiment 4, the sheath 20 has the protrusion 4 and the protrusion 5 provided on two positions which are spaced out from each other in a longitudinal direction on the inner peripheral surface thereof.

Therefore, according to the medical needle device according to the embodiment 4, since the sheath 20 has the protrusion 4 and the protrusion 5 provided on two positions which are spaced out from each other in the longitudinal direction on the inner peripheral surface thereof, the protrusion 4 and the protrusion 5 on the sheath 20 abut the outer peripheral surface of the hub 10 at two positions in the longitudinal direction, thereby stably holding the outer peripheral surface of the hub 10. The protrusions may also be provided on a plurality of positions not less than three.

Next, referring to FIG. 16, a medical needle device according to embodiment 5 will be described.

Figure 16:
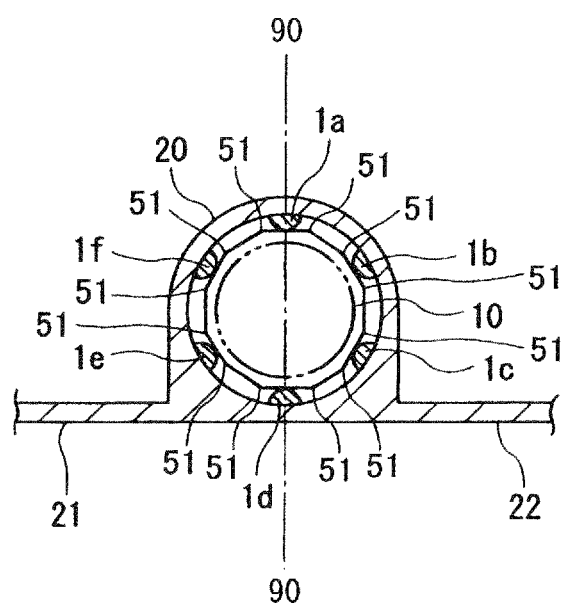
FIG. 16 is a cross section of the sheath of the medical needle device according to embodiment 5 of the present invention.

FIG. 16 is a cross section of the sheath 20 of the medical needle device according to embodiment 5 of the present invention, which corresponds to a I-I line enlarged cross section of FIG. 12.

Figure 17:
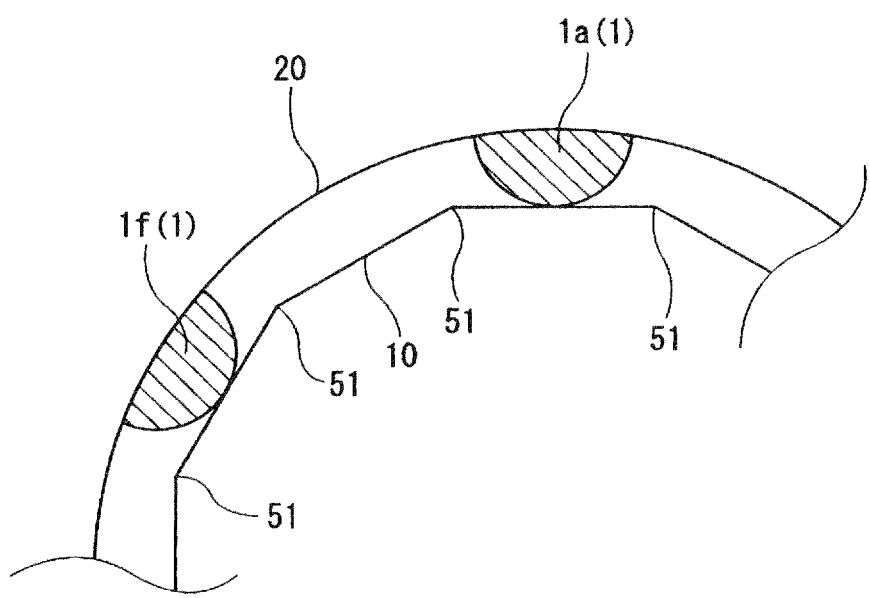
FIG. 17 is an enlarged cross section of important parts of FIG. 16.
Figure 18:
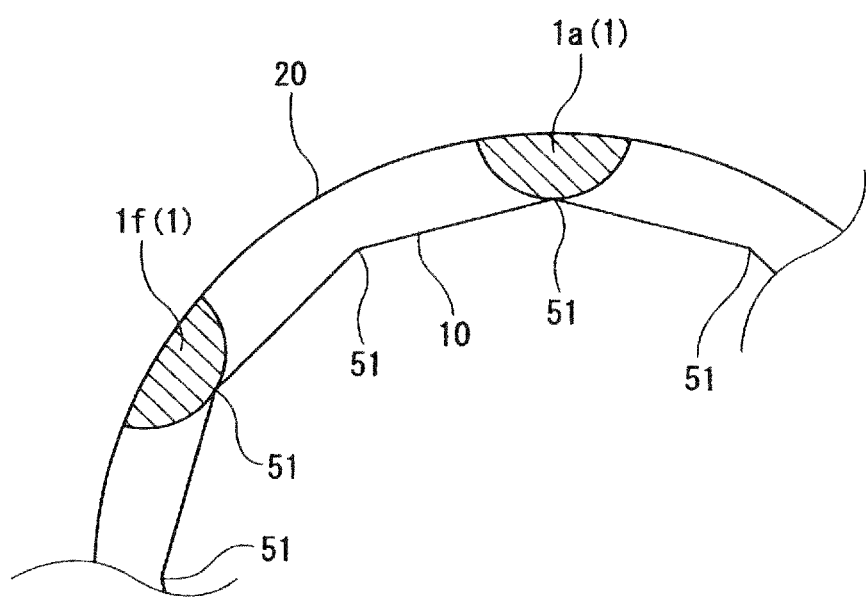
FIG. 18 is an enlarged cross section of important parts of a state that protrusions on the sheath of the medical needle device of FIG. 16 abut convexes.

The hub 10 of the medical needle device of the embodiment 1, which the protrusions 1 provided on the inner peripheral surface of the sheath 20 abut is circular in cross section whereas the hub 10 of the embodiment 5, which the protrusions 1 (1a to 1f) abut is polygonal in cross section by forming a plurality of convexes 51 along the outer peripheral surface of the hub 10 so that the protrusions 1 abut the convexes 51 when the hub 10 transfers in the rotational direction relative to the sheath 20. FIG. 17 shows a state before the protrusions 1 abut the convexes 51 whereas FIG. 18 shows a state that the protrusions 1 abut the convexes 51.

In the present embodiment, the polygon is a regular dodecagon of which each of the twelve corners form a plurality of convexes 51 and number of the protrusions 1 (1a to 1f) which abut the convexes 51 is six.

Each surface of the polygon (a line connecting two adjacent convexes 51) is provided on a position where the surface comes into contact with the outer peripheral surface of the hub 10 of the medical needle device according to the embodiment 1 from the outside. More specifically, a diameter of a set of the points where each of the surfaces forming the polygon abut the outer peripheral surface of the hub 10 is the same as an outside diameter of the hub 10, a diameter of the corners forming the convexes 51 is larger than the outside diameter of the hub 10 and the corners are positioned outside compared with the outer peripheral surface of the hub 10.

According to the structure, when the force is applied on the hub 10 in the rotational direction relative to the sheath 20, the protrusions 1 in point contact with the outer peripheral surface of the hub 10 abut the convexes 51 positioned outside compared with the outer peripheral surface of the hub 10 so that the fitting force increases for projection of the convexes 51, thereby increasing the rotational torque.

Such a structure prevents unexpected rotation of the hub 10 relative to the sheath 20, caused by weight of a forceps (not shown) which fastens the tube 40 for infusions or blood transfusions, connected to the rear end 10b of the hub 10 so as to blockade watercourse of the tube 40.

In addition, such a structure enables to set the projecting height and elastic force of the convexes 51 as follows. As shown in FIG. 18, the projecting height and elastic force of the convexes 51 prevent the hub from rotating relative to the sheath 20 in case the rotational torque less than certain amount T is applied on the hub 10 in a state in which the protrusions 1 abut the convexes 51 whereas the projecting height and the elastic force of the convexes 51 allow the protrusions 1 to climb over the convexes 51 so that the hub 10 rotates relative to the sheath 20 in case the rotational torque not less than the certain amount T, for example the rotational torque of not less than 0.3 cN·m (rotational operation force), is applied on the hub 10 in the state in which the protrusions 1 abut the convexes 51.

Therefore, when the certain amount T is set to be larger than weight of the forceps and the force required for normal operation within a manually operatable range for a user (doctor or nurse), unexpected rotation of the hub relative to the sheath, caused by the weight of the forceps is prevented and a manual operation of the user can obtain the fitting force of the hub with the sheath to the maximum on a point just before the certain amount T.

In the present embodiment, the polygon is the regular dodecagon and number of the corners (12) is twice which is a multiple of the number of the protrusions 1 (6) provided on the inner peripheral surface of the sheath 20 at regular intervals. But the multiple is not restricted to twice and may also be integer multiples of not less than 1 or fractional multiples from 0 to 1.

The outer peripheral surface of the hub 10 which the protrusions abut is polygonal in cross-section, of which each of the corners form a plurality of convexes 51. Accordingly, a rotational operation to attain certain angle is carried out by rotating the hub 10 relative to the sheath 20 so that the protrusions 1 abut the convexes 51 and applying the certain amount T as further force in the rotational direction so that the convexes 51 press the protrusions 1 outward, the protrusions 1 climb over the convexes 51 and the protrusions 1 abut the adjacent convexes 51 spaced out from the former convexes 51. The rotational torque (rotational operation force) not less than certain amount T required for the protrusions 1 to climb over the convexes 51 is recognized by the user as a tactile signal (sense of click). Corner-shaped convexes 51 transmit a sharper tactile signal (sense of click) than round-shaped convexes without corners (for example convexes 52 shown in FIG. 19 and described later).

The tactile signal (sense of click) enables the user to recognize a position of the hub 10 on the rotational direction relative to the sheath 20 by the sense of touch as well as sight. Especially, the cross-section regular polygonal outer peripheral surface of the hub 10 and the protrusions 1 provided at regular intervals as described in the embodiment 5 enables relatively easy positioning of the hub 10 on a desired phase relative to the sheath 20.

As shown in FIG. 16, the cross-section regular dodecagon outer peripheral surface of the hub 10 and six protrusions 1 provided on the inner peripheral surface of the sheath 20 at regular intervals enable the hub 10 to rotate relative to the sheath 20 by a rotational angle of 30 degrees for the effect of the rotational torque (rotational operation force) not less than certain amount T, which transmits the tactile signal (sense of click) every 30 degrees. Accordingly, three consecutive times of the rotational operation of 30 degrees results in an accurate rotational operation of 90 degrees.

Some of the medical needle device products include an erroneous piercing prevention mechanism in which an injection needle 11 fit on the top end of the hub 10 is pulled back and stored inside the sheath 20 after use. A pull-back operation of the products is carried out upon matching phase between convexes (not shown) provided on an outer peripheral part of the hub 10 and fitting concaves (not shown) provided on the inner peripheral part of the sheath 20. As shown in FIGS. 8 and 9, in case edge of the injection needle 11 faces front-upward and the wings 21, 22 mounted on the sheath 20 face upward, the convexes on the hub 10 are deflected by 90 degrees in the rotational direction, to the right for example, relative to the fitting concaves on the sheath 20 so that the pull-back operation can not be carried out whereas in case the hub 10 is rotated to the left by 90 degrees relative to the sheath 20 so as to match the convexes on the hub 10 and the fitting concaves on the sheath 20, the injection needle 11 fit on the top end of the hub 10 can be pulled back and stored inside the sheath 20.

According to the medical needle device of the embodiment 1, it is necessary to visually confirm the position of the edge of the injection needle 11 while rotating the hub 10 relative to the sheath 20 so as to match the convexes on the hub 10 and the fitting concaves on the sheath 20, which requires attention to be paid in positioning.

On the other hand, according to the medical needle device of the embodiment 5, three consecutive times of the rotational operation of 30 degrees with the tactile signal (sense of click) results in the accurate rotational operation of 90 degrees. Therefore, the phase between the convexes on the hub 10 and the fitting concaves on the sheath 20 can be matched accurately, safely and extremely easily so as to pull back and store the injection needle 11 inside the sheath 20.

Next, referring to FIG. 19, a medical needle device according to embodiment 6 will be described.

Figure 19:
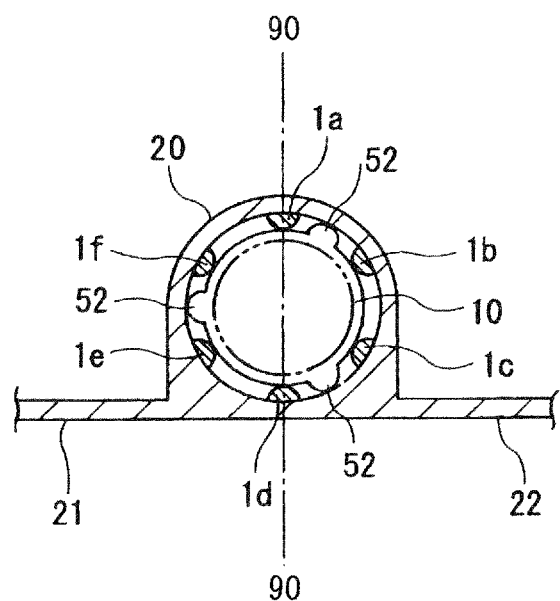
FIG. 19 is a cross section of the sheath of the medical needle device according to embodiment 6 of the present invention.

FIG. 19 is a cross section of the sheath 20 of the medical needle device according to the embodiment 6 of the present invention, which corresponds to a I-I line enlarged cross section of FIG. 12.

According to the medical needle device of the embodiment 5, the convexes 51 provided on the outer peripheral surface of the hub 10 have projecting height which does not abut the inner peripheral surface of the sheath 20 in the state in which the protrusions 1 provided on the inner peripheral surface of the sheath 20 do not abut the convexes 51 whereas according to the medical needle device of the embodiment 6, the convexes 52 have the projecting height which abuts the inner peripheral surface of the sheath 20 in the state in which the protrusions 1 do not abut the convexes 52.

In the present embodiment, the hub 10 has three convexes 52 without corners provided on the outer peripheral surface of the hub 10 at regular intervals. The cross sectional shape of the convexes 52 is semicircular in the same manner as the cross sections of the protrusions 1, which protrude in a opposite direction from the protrusions 1, in another word, toward the sheath 20.

The convexes 52 have projecting height which abuts the inner peripheral surface of the sheath 20 at a vertex thereof in the state ill which the protrusions 1 do not abut the convexes 52 as shown in FIG. 19.

Figure 20A:
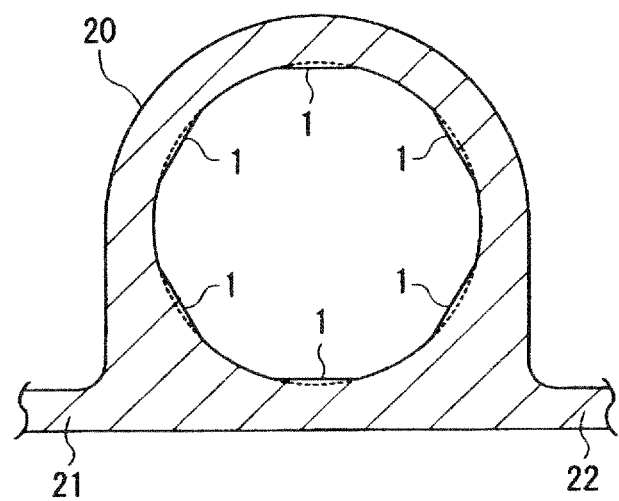
FIGS. 20 (*a*) to (*c*) are cross sections of hubs and sheaths of another medical needle device according to embodiment 6 of the present invention.
Figure 20B:
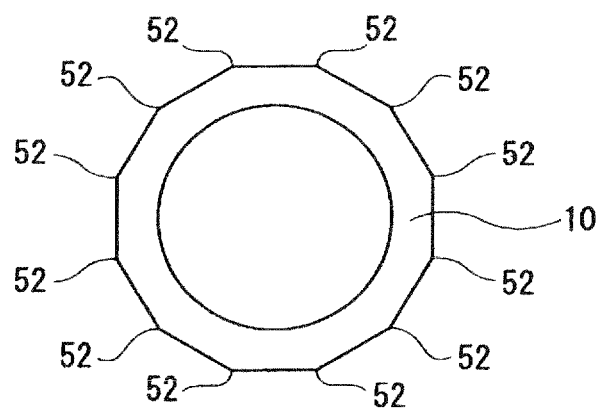
Figure 20C:
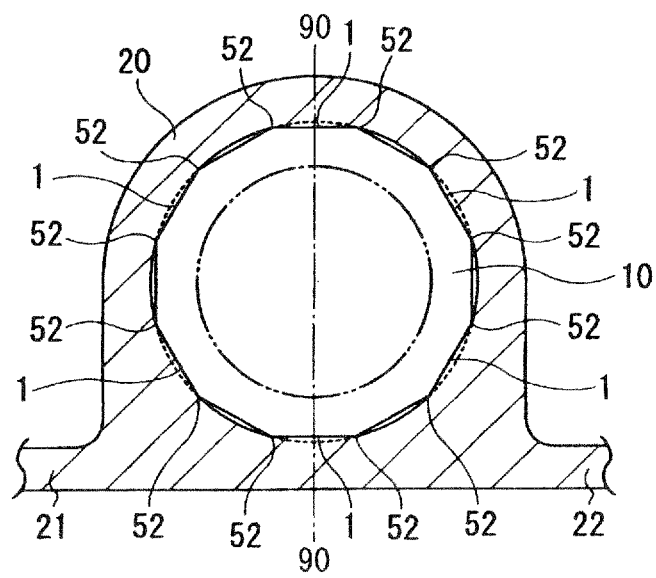

Cross sectional shape, number or intervals of the convexes 52 are not strictly restricted. As shown in FIG. 20, the convexes 52 may have corners in cross section, which abut the inner peripheral surface of the sheath 20 in the state in which the protrusions 1 do not abut the convexes 52.

FIGS. 20 (a) to (c) are cross sections showing hubs 10 and sheaths 20 of another medical needle device according to embodiment 6, where (a) shows a section of the sheath 20, (b) shows a section of the hub 10 and (c) shows a section of a state in which the sheath 20 is fit on the hub 10. The sheath 20 has six protrusions 1 provided on the inner peripheral surface thereof, which are spaced out from each other at regular intervals.

The protrusions 1 on the sheath 20 are prepared by dividing the circular inner peripheral surface of the sheath 20 into twelve equal parts and then alternately preparing six segments linking two adjacent corners by lines and six arc parts where two adjacent corners are not linked so as to regard the six segments linking two adjacent corners by lines as protrusions 1 protruding inward. On the other hand, the convexes 52 are prepared by forming the outer peripheral surface of the hub 10 into a regular dodecagon of which each corner forms a plurality of (twelve) the convexes 52. One side of the regular dodecagon as the outer peripheral surface of the hub 10 equals length of the segment (linking two adjacent corners by lines) as the protrusions 1. Accordingly, as shown in FIG. 20 (c), when the sheath 20 is fit on the hub 10 and the protrusions 1 on the sheath 20 do not abut the convexes 52 of the hub 10, every other side of the regular dodecagon as the outer peripheral surface of the hub 10 matches the segments as the protrusions 1 on the sheath 20. When the force is applied on the hub 10 relative to the sheath 20 in aforesaid state in the rotational direction, the protrusions 1 on the sheath 20 abut the convexes 52 on the hub 10. Further, when the force not less than the certain amount T is applied on the hub 10, the protrusions 1 on the sheath 20 climb over the convexes 52 on the hub 10.

According to the structure, since the convexes 52 abut the inner peripheral surface of the sheath 20 in a state in which the protrusions 1 do not abut the convexes 52, fitting force generating from abutting of the convexes 52 against the inner peripheral surface of the sheath 20 as well as the fitting force required for the protrusions 1 to climb over the convexes 52 on the hub 10 increase the fitting force between the hub 10 and the sheath 20, thereby improving the rotational torque.

Such a structure prevents unexpected rotation of the hub 10 relative to the sheath 20, which enables a stable operation of the medical needle device.

We claim:

1. A medical needle device comprising:
    a hub having an injection needle fixed at a top end thereof; and
    a substantially cylindrical sheath which is fitted on the hub and which has first and second wings mounted on respective sides thereof, said first and second wings being bent along the respective sides of said sheath, overlapped, and held together at a time of puncturing so that an inner peripheral surface of said sheath strongly presses an outer peripheral surface of said hub, thereby preventing movement of said hub caused by transfer of the hub relative to said sheath in both a rotational direction and a longitudinal direction;
    wherein said sheath has a plurality of protrusions provided on the inner peripheral surface thereof in a circumferential direction, said protrusions being spaced out from each other;
    wherein the outer peripheral surface of said hub abuts said protrusions and has a shape of a polygon in cross section;
    wherein said hub which said protrusions abut has a plurality of convexes formed along the outer peripheral surface thereof, and corners of said polygon form said plurality of convexes;
    wherein after the time of puncturing, said first and second wings are no longer held together and the inner peripheral surface of said sheath no longer presses the outer peripheral surface of said hub; and
    wherein said hub is translatable in a rotational direction relative to said sheath after the time of puncturing so that said protrusions abut said convexes and are able to climb over said convexes when said hub translates in the rotational direction relative to said sheath after the time of puncturing.

2. The medical needle device as claimed in claim 1, wherein:
    said polygon is a regular polygon having a number of corners corresponding to a multiple of a number of said protrusions provided on the inner peripheral surface of said sheath, said protrusions being spaced out at regular intervals.

3. The medical needle device as claimed in claim 2, wherein:
    said polygon is a regular dodecagon; and
    the number of said protrusions is six.

4. The medical needle device as claimed in claim 1, wherein:
    said convexes have a projecting height such that said convexes do not abut the inner peripheral surface of said sheath when in a state in which said protrusions do not abut said convexes.

5. The medical needle device as claimed in claim 1, wherein:
    said convexes have a projecting height such that said convexes abut the inner peripheral surface of said sheath when in a state in which said protrusions do not abut said convexes.

6. The medical needle device as claimed in claim 1, wherein:
    a projecting height and an elastic force of said convexes are set such that said hub is prevented from rotating relative to said sheath when rotational torque less than a predetermined amount is applied on said hub when in a state in which said protrusions abut said convexes, and
    the projecting height and the elastic force of said convexes are set such that said protrusions are able to climb over said convexes so that said hub rotates relative to said sheath when rotational torque not less than the predetermined amount is applied on said hub in the state in which said protrusions abut said convexes.

* * * * *